United States Patent
Voit et al.

(10) Patent No.: US 7,091,153 B2
(45) Date of Patent: Aug. 15, 2006

(54) HYDROGENATION CATALYST

(75) Inventors: Guido Voit, Freinsheim (DE); Rolf Fischer, Heidelberg (DE); Peter Bassler, Viernheim (DE); Andreas Ansmann, Wiesloch (DE); Hermann Luyken, Ludwigshafen (DE); Martin Merger, Frankenthal (DE); Frank Ohlbach, Dossenheim (DE); Alwin Rehfinger, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 165 days.

(21) Appl. No.: 10/776,544

(22) Filed: Feb. 12, 2004

(65) Prior Publication Data

US 2004/0181095 A1  Sep. 16, 2004

Related U.S. Application Data

(62) Division of application No. 09/851,214, filed on May 8, 2001, now Pat. No. 6,852,669, which is a division of application No. 09/622,773, filed as application No. PCT/EP99/01150 on Feb. 23, 1999, now Pat. No. 6,297,394.

(30) Foreign Application Priority Data

Mar. 6, 1998 (DE) ................................ 198 09 687

(51) Int. Cl.
*B01J 23/34* (2006.01)
*B01J 21/14* (2006.01)

(52) U.S. Cl. ........................ 502/324; 502/241; 502/243
(58) Field of Classification Search ................ 502/324, 502/241, 243
See application file for complete search history.

(56) References Cited

U.S. PATENT DOCUMENTS

| | | | |
|---|---|---|---|
| 3,696,153 A | 10/1972 | Kershaw et al. | 260/583 |
| 3,986,985 A | 10/1976 | Dewdney et al. | 252/472 |
| 4,064,172 A | 12/1977 | Dewdney et al. | 260/583 |
| 4,282,381 A | 8/1981 | Bühler et al. | 564/498 |
| 5,527,946 A | 6/1996 | Flick et al. | 558/459 |
| 5,935,897 A * | 8/1999 | Trubenbach et al. | 502/150 |
| 6,222,059 B1 | 4/2001 | Ebel et al. | 558/459 |

FOREIGN PATENT DOCUMENTS

| | | |
|---|---|---|
| DE | 848 654 | 9/1952 |
| DE | 24 29 293 | 3/1975 |
| WO | WO 96/20166 | 7/1996 |
| WO | WO 98/11059 | 3/1998 |

OTHER PUBLICATIONS

Weissermel, Arpe, Industrielle Organsiche Chemie, Verlag Chemie, 3rd Edition (1988), p. 266.

* cited by examiner

*Primary Examiner*—Johann Richter
*Assistant Examiner*—Ebenezer Sackey
(74) *Attorney, Agent, or Firm*—Novak Druce & Quigg, LLP; S. Peter Konzel

(57) ABSTRACT

A material useful as catalyst for the hydrogenation of alpha, omega-dinitriles comprises
(a) iron or a compound based on iron or mixtures thereof,
(b) from 0.001 to 0.3% by weight based on (a) of a promoter based on 2, 3, 4 or 5 elements selected from the group consisting of aluminum, silicon, zirconium, titanium and vanadium,
(c) from 0 to 0.3% by weight based on (a) of a compound based on an alkali and/or alkaline earth metal, and also
(d) from 0.001 to 1% by weight based on (a) of manganese.

16 Claims, No Drawings

HYDROGENATION CATALYST

CROSS-REFERENCE TO RELATED APPLICATION(S)

This is a Divisional application of application Ser. No. 09/851,214, filed on May 8, 2001 now U.S. Pat. No. 6,852,669, the entire disclosure of which is herewith incorporated by reference, which is a Divisional application of application Ser. No. 09/622,773, filed on Aug. 23, 2000 (now U.S. Pat. No. 6,297,394 B1), the entire disclosure of which is herewith incorporated by reference, which is a National Stage Application under 35 U.S.C. 371 based on International Application No. PCT/EP 99/01150, filed on Feb. 23, 1999.

The present invention relates to a material useful as catalyst, comprising
(a) iron or a compound based on iron or mixtures thereof,
(b) from 0.001 to 0.3% by weight based on (a) of a promoter based on 2, 3, 4 or 5 elements selected from the group consisting of aluminum, silicon, zirconium, titanium and vanadium,
(c) from 0 to 0.3% by weight based on (a) of a compound based on an alkali and/or alkaline earth metal, and also
(d) from 0.001 to 0.3% by weight based on (a) of manganese.

The present invention further relates to processes for hydrogenation of aliphatic alpha, omega-dinitriles in the presence of such materials as catalyst and to the use of such materials as catalyst in the hydrogenation of aliphatic alpha, omega-dinitriles.

It is commonly known, for example from Weissermel/Arpe, Industrielle Organische Chemie, Verlag Chemie, third edition, 1988, page 266, and WO-A-96/20166 to hydrogenate adiponitrile in the presence of ammonia under high pressure conditions over predominantly iron catalysts to form 6-aminocapronitrile and/or hexamethylenediamine, which are both important intermediates for the manufacture of polyamides such as nylon-6 and nylon-6,6.

Important requirements for good iron catalysts include high mechanical strength, a long time on stream, a high space-time yield of the products of value, alpha, omega-aminonitrile and/or alpha, omega-diamine, coupled with complete alpha, omega-dinitrile conversion and a very low level of unwanted by-products.

These unwanted by-products are formed in varying amounts, depending on the catalyst, and are difficult to separate from the desired aminonitrile and/or diamine product.

For instance, the hydrogenation of adiponitrile to hexamethylenediamine by-produces varying quantities of, inter alia, tetrahydroazepine (THA), 1-amino-2-cyanocyclopentene (ICCP), 2-aminomethylcyclopentylamine (AMCPA), 1,2-diaminocyclohexane (DCH) and bishexamethylenetriamine (BHMTA). U.S. Pat. No. 3,696,153 discloses that AMCPA and DCH are very difficult to separate from hexamethylenediamine. Notably large amounts of AMCPA, DCH and THA necessitate a great deal of distillation, which is reflected in considerable capital and energy costs.

U.S. Pat. No. 4,282,381, column 2, Table 1, discloses that the hydrogenation of adiponitrile to hexamethylenediamine in the presence of iron catalysts by-produces inter alia on average from 2400 to 4000 ppm of 1,2-diaminocyclohexane, from 100 to 300 ppm of 2-aminomethylcyclopentylamine, from 200 to 900 ppm of tetrahydroazepine and from 2000 to 5000 ppm of 6-aminocapronitrile.

DE-A-2 429 293 discloses in Example 1 that the hydrogenation of adiponitrile in the presence of five times the weight of ammonia at from 93 to 985 C (inlet temperature into the reactor) or at from 94 to 1045 C (outlet temperature) over an iron catalyst prepared from magnetite by reduction with hydrogen and doped with aluminum oxide, silicon dioxide, calcium oxide and vanadium pentoxide yields 98.22% of hexamethylenediamine comprising 1900 ppm of 1,2-diaminocyclohexane, and in Example 2 that the hydrogenation of adiponitrile in the presence of five times the weight of ammonia at from 93 to 985 C (inlet temperature into the reactor) or at from 94 to 1045 C (outlet temperature) over an iron catalyst prepared from Labrador hematite ore ($Fe_2O_3$) by reduction with hydrogen and doped with aluminum oxide, silicon dioxide and calcium oxide yields 98.05% of hexamethylenediamine comprising 3500 ppm of 1,2-diaminocyclohexane.

It is an object of the present invention to provide processes for hydrogenating alpha, omega-dinitriles (I) to alpha, omega-aminonitriles (II) and/or alpha, omega-diamines (III) in the presence of a catalyst and also catalysts without the disadvantages mentioned and with the capability of enabling the hydrogenation of alpha, omega-dinitriles to be carried out with high selectivity in a technically simple and economical manner with a long time on stream of the catalyst.

We have found that this object is achieved by the materials defined at the beginning, the process defined at the beginning and the use defined at the beginning.

The materials of the invention preferably have a BET surface area of from 3 to 20 $m^2$/g, a total pore volume of from 0.05 to 0.2 mL/g, an average pore diameter of from 0.03 to 0.1 μm and a 0.01 to 0.1 μm pore volume fraction within the range from 50 to 70%.

The weight % ages in (b) and (d) are based on the elements and the weight % ages in (c) are based on the oxides of the alkali and alkaline earth metals. These percentages are based on component (a).

In preferred catalyst precursors, component (a) comprises from 90 to 100% by weight, preferably from 92 to 99% by weight, based on (a), of iron oxides, iron hydroxides, iron oxyhydroxides or mixtures thereof. Preference is given to using synthesized or naturally occurring iron oxides, iron hydroxides or iron oxyhydroxides, such as limonite, hematite, preferably magnetite, which in the ideal case can be described using the formula $Fe_3O_4$. The atomic ratio of oxygen to iron is preferably within the range from 1.25:1 to 1.45:1, preferably within the range from 1.3:1 to 1.4:1, particularly preferably equal to 1.33:1, i.e., pure magnetite.

If magnetite is synthesized, it is possible to start from very pure metallic iron or from very pure iron(II) compounds and/or iron(III) compounds, to which the doping elements are added subsequently in the form of suitable compounds.

Preference is further given to catalyst precursors in which component (b) comprises from 0.001 to 0.3% by weight, preferably from 0.01 to 0.2% by weight, especially from 0.01 to 0.1% by weight, of a promoter based on 2, 3, 4 or 5, preferably 3, 4 or 5, elements selected from the group consisting of aluminum, zirconium, silicon, titanium and vanadium, especially the combination of aluminum, silicon and titanium.

Preference is further given to catalyst precursors in which component (c) comprises from 0 to 0.3% by weight, preferably from 0.01 to 0.2% by weight, particularly preferably from 0.01 to 0.1% by weight, of a compound based on an alkali or alkaline earth metal selected from the group consisting of lithium, sodium, potassium, rubidium, cesium, magnesium and calcium, preferably calcium and/or magnesium.

The materials of the invention comprise from 0.001 to 1% by weight, preferably from 0.001 to 0.3% by weight, especially from 0.01 to 0.2% by weight, of manganese.

The catalysts of the invention can be supported or unsupported catalysts. Examples of possible support materials are porous oxides such as aluminum oxide, silicon dioxide, alumosilicates, lanthanum oxide, titanium dioxide, zirconium dioxide, magnesium oxide, zinc oxide, and zeolites and also activated carbon or mixtures thereof.

Preparation is generally effected by precipitating one or more precursors of component (a) if desired together with precursors of promoter components (b), (d) and if desired with precursors of components (c) in the presence or absence of support materials (depending on which catalyst type is desired), if desired processing the resulting catalyst precursor into extrudates or tablets, drying and then calcining. Supported catalysts are generally also obtainable by saturating the support with a solution of components (a), (b), (d) and if desired (c), it being possible to add the individual components simultaneously or in succession, or by spraying the components (a), (b), (d) and if desired (c) onto the support in a conventional manner.

Suitable precursors for components (a) are generally readily water-soluble salts of iron such as nitrates, chlorides, acetates, formates and sulfates, preferably nitrates.

Suitable precusors for components (b) and (d) are generally readily water-soluble salts or complexes of the aforementioned metals and semimetals such as nitrates, chlorides, acetates, formates and sulfates, preferably nitrates.

Suitable precursors for components (c) are generally readily water-soluble salts of the aforementioned alkali metals and alkaline earth metals such as hydroxides, carbonates, nitrates, chlorides, acetates, formates and sulfates, preferably hydroxides and carbonates.

Precipitation is generally effected from aqueous solutions, selectively by adding precipitating reagents, by changing the pH or by changing the temperature.

The catalyst prematerial thus obtained is customarily dried at a temperature generally within the range from 80 to 1505 C, preferably within the range from 80 to 1205 C Calcining is customarily effected at a temperature within the range from 150 to 5005 C, preferably within the range from 200 to 4505 C, in a gas stream of air or nitrogen.

After calcining, the catalyst material obtained is generally exposed to a reducing atmosphere ("activation"), for example by exposing it at a temperature within the range from 200 to 5005 C, preferably within the range from 250 to 4005 C, to a hydrogen atmosphere or a gas mixture comprising hydrogen and an inert gas such as nitrogen for a period within the range from 2 to 24 hours. The volume hourly space velocity for this is preferably 200 L per liter of catalyst per hour.

According to DE 24 29 293 (page 7, lines 1 to 12), it can be advantageous to add ammonia to the activating hydrogen.

Advantageously, the activation of the catalyst is carried out directly in the synthesis reactor, since this customarily obviates an otherwise necessary intermediary step, namely the passivation of the surface by means of oxygen-nitrogen mixtures such as air at a temperature which is customarily within the range from 20 to 805 C, preferably within the range from 25 to 355 C The activation of passivated catalysts is then preferably carried out in the synthesis reactor in a hydrogen-comprising atmosphere at a temperature within the range from 180 to 5005 C, preferably within the range from 200 to 3505 C The catalysts can be used as fixed bed catalysts in upflow or trickle mode or as suspension catalysts.

The starting materials used in the process of the present invention are aliphatic alpha, omega-dinitriles of the general formula I NC—(CH$_2$)$_n$—CN    I where n is an integer from 1 to 10, especially 2, 3, 4, 5 or 6. Particularly preferred compounds I are succinonitrile, glutaronitrile, adiponitrile, pimelonitrile and suberonitrile, most preferably adiponitrile.

Particular preference is given to using alpha, omega-dinitriles obtained by hydrocyanation in the presence of phosphorus catalysts of an alpha, omega-diene having two carbon atoms fewer, such as adiponitrile by addition of hydrocyanic acid to butadiene or 3-pentenenitrile in the presence of nickel(0) compounds and triaryl phosphites.

Such alpha, omega-dinitriles may comprise traces of phosphorus compounds, from about 1 to 50 ppm, reckoned as phosorus and based on alpha, omega-dinitrile. Removing these phosphorus compounds in whole or in part to obtain weight fractions of phosphorus compound of less than 5 ppm, preferably less than 1 ppm, makes it possible to raise the long catalyst times on stream obtained in the process of the invention and in the use of the invention even further.

To reduce the weight fraction of phosphorus compound in the mixture various conventional processes, such as precipitation, preferably extraction, treatment with a base such as sodium hydroxide solution or potassium hydroxide solution, adsorption or chemisorption, especially on a metal such as iron or, particularly preferably, distillation come into consideration. Particular preference is also given to the treatment of the dinitrile with metal bases of the alkali and alkaline earth metal group, of the lanthanides and of groups III a, II b and III b of the periodic table, e.g., calcium oxide.

The distillation can advantageously be carried out at a pressure of from 1 to 100 mbar, preferably of from 10 to 200 mbar, in which case the adiponitrile is usually obtained as overhead product, since the phosphorus compounds are essentially less volatile than adiponitrile.

The process of the present invention can hydrogenate the above-described dinitriles I by means of a catalyst, preferably in the presence of a solvent, to alpha, omega-aminonitriles of the general formula II

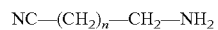

NC—(CH$_2$)$_n$—CH$_2$—NH$_2$    II where n is as defined above. Particularly preferred aminonitriles II are those in which n is 2, 3, 4, 5 or 6, especially 4, i.e., 4-aminobutanenitrile, 1,5-aminopentanenitrile, 1,6-aminohexanenitrile ("6-aminocapronitrile"), 1,7-aminoheptanenitrile and 1,8-aminooctanenitrile, most preferably 6-aminocapronitrile.

If the reaction is carried out in suspension, the temperature will be customarily selected from within the range from 40 to 1505 C, preferably from within the range from 50 to 1005 C, particularly preferably from within the range from 60 to 905 C The pressure is generally chosen from within the range from 2 to 30 Mpa, preferably from within the range from 3 to 30 Mpa, particularly preferably from within the range from 4 to 9 Mpa. The residence time is essentially dependent on the desired yield, selectivity and if conversion is complete; the residence time may customarily be chosen so as to obtain maximum yield at complete conversion, for example from within the range from 50 to 275 min, preferably from within the range from 70 to 200 min.

The suspension process solvent is preferably selected from ammonia, amines, diamines and triamines having from 1 to 6 carbon atoms such as trimethylamine, triethylamine, tripropylamine and tributylamine or alcohols, especially methanol and ethanol, and is particularly preferably ammonia. The dinitrile concentration is advantageously chosen from within the range from 10 to 90% by weight, preferably from within the range from 30 to 80% by weight, particularly preferably from within the range from 40 to 70% by weight, based on the sum total of dinitrile and solvent.

The amount of catalyst is generally chosen so that the catalyst quantity is within the range from 1 to 50% by weight, preferably within the range from 5 to 20% by weight, based on the amount of dinitrile used.

The suspension hydrogenation can be carried out batchwise or, preferably, continuously, generally in the liquid phase.

The hydrogenation can also be carried out batchwise or continuously in a fixed bed reactor in trickle or upflow mode with a straight pass or with product recycling, in which case it is customary to select a temperature from within the range from 20 to 1505 C, preferably from within the range from 30 to 905 C, and a pressure generally from within the range of from 2 to 40 Mpa, preferably from within the range from 3 to 30 Mpa. The hydrogenation is preferably carried out in the presence of a solvent, preferably ammonia, amines, diamines and triamines, having from 1 to 6 carbon atoms, such as trimethylamine, triethylamine, tripropylamine and tributylamine, or alcohol, preferably methanol and ethanol, particularly preferably ammonia. In a preferred embodiment, the ammonia content is within the range from 1 to 10 g, preferably within the range from 2 to 6 g, per gram of adiponitrile. Preference is given to using in this embodiment a catalyst space velocity which is within the range from 0.1 to 2.0 kg, preferably within the range from 0.3 to 1.0 kg, of adiponitrile/L×h. Here, too, the residence time can be varied to adjust the conversion in a specific manner.

The hydrogenation can be carried out in a customary hydrogenation reactor.

The ratio of aminonitriles (II) to diamines (III) can be controlled through specific choice of temperature and catalyst space velocity.

The hydrogenation of adiponitrile as alpha, omega-dinitrile affords a mixture which, as well as the solvent, very predominantly comprises 6-aminocapronitrile, hexamethylenediamine and unconverted adiponitrile, which may include especially hexamethyleneimine, 2-aminomethylcyclopentylamine, 1,2-diaminocyclohexane, tetrahydroazepine and bishexanemethylenetriamine as impurities.

The removal of 6-aminocapronitrile, hexamethylenediamine and an essentially adiponitrile portion from the mixture can be effected in a conventional manner, preferably by distillation, for example as described in DE-A-19 500 222 or German Application 19 548 289.1, simultaneously or in succession.

The process of the invention can hydrogenate the above-described dinitriles I by means of a catalyst, preferably in the presence of a solvent, to alpha, omega-diamines of the general formula III

$$H_2N-CH_2-(CH_2)_n-CH_2-NH_2 \qquad III$$

where n is as defined above. Particularly preferred diamines III are those in which n is 2, 3, 4, 5 or 6, especially 4, i.e., 4-diaminobutane, 1,5-diaminopentane, 1,6-diaminohexane ("hexamethylenediamine"), 1,7-diaminoheptane and 1,8-diaminooctane, most preferably 1,6-diaminohexane.

If the reaction is carried out in suspension, the temperature will be customarily selected from within the range from 60 to 2005 C, preferably from within the range from 60 to 1805 C, particularly preferably from within the range from 70 to 1305 C The pressure is generally chosen from within the range from 2 to 30 Mpa, preferably from within the range from 3 to 30 Mpa, particularly preferably from within the range from 4 to 20 Mpa. The residence time is essentially dependent on the desired yield and selectivity if conversion is complete; the residence time may customarily be chosen so as to obtain maximum yield at complete conversion, for example from within the range from 50 to 300 min, preferably from within the range from 70 to 200 min.

The suspension process solvent is preferably selected from ammonia, amines, diamines and triamines having from 1 to 6 carbon atoms such as trimethylamine, triethylamine, tripropylamine and tributylamine or alcohols, especially methanol and ethanol, and is particularly preferably ammonia.

The dinitrile concentration is advantageously chosen from within the range from 10 to 90% by weight, preferably from within the range from 30 to 80% by weight, particularly preferably from within the range from 40 to 70% by weight, based on the sum total of dinitrile and solvent.

The amount of catalyst is generally chosen so that the catalyst quantity is within the range from 1 to 50% by weight, preferably within the range from 5 to 20% by weight, based on the amount of dinitrile used.

The suspension hydrogenation can be carried out batchwise or, preferably, continuously, generally in the liquid phase.

The hydrogenation can also be carried out batchwise or continuously in a fixed bed reactor in trickle or upflow mode with a straight pass or with product recycling, in which case it is customary to select a temperature from within the range from 70 to 2005 C, preferably from within the range from 80 to 1505 C, and a pressure generally from within the range of from 2 to 40 Mpa, preferably from within the range from 3 to 30 Mpa. The hydrogenation is preferably carried out in the presence of a solvent, preferably ammonia, amines, diamines and triamines, having from 1 to 6 carbon atoms, such as trimethylamine, triethylamine, tripropylamine and tributylamine, or alcohol, preferably methanol and ethanol, particularly preferably ammonia. In a preferred embodiment, the ammonia content is within the range from 1 to 10 g, preferably within the range from 2 to 6 g, per gram of adiponitrile. Preference is given to using in this embodiment a catalyst space velocity which is within the range from 0.1 to 2.0 kg, preferably within the range from 0.3 to 1.5 kg, of adiponitrile/L×h. Here, too, the residence time can be varied to adjust the conversion in a specific manner.

The hydrogenation can be carried out in a customary hydrogenation reactor.

The hydrogenation of adiponitrile as alpha, omega-dinitrile affords a mixture which, as well as the solvent, very predominantly comprises hexamethylenediamine, which may include especially 6-aminocapronitrile, hexamethyleneimine, 2-aminomethylcyclopentylamine, 1,2-diaminocyclohexane, tetrahydroazepine and bishexanemethylenetriamine as impurities.

The purification of the crude hexamethylenediamine obtained after removal of the solvent is in general preferably effected by distillation.

alpha, omega-Aminonitriles and alpha, omega-diamines are important starting compounds for producing nylon-6,6 and/or nylon-6.

IN THE EXAMPLES

ADN=adiponitrile
ACN=6-aminocapronitrile
HMD=hexamethylenediamine
DCH=1,2-diaminocyclohexane
AMCPA=2-aminomethylcyclopentylamine
BHMTA=bishexamethylenetriamine
ICCP=1-amino-2-cyanocyclopentene
THA=tetrahydroazepine
HMI=hexamethyleneimine The analytical values in the table were obtained by quantitative gas chromatography.

Example 1 a) Catalyst Preparation

The catalyst was prepared by heating a magnetite ore under nitrogen at 1500° C for six hours. The magnetite ore used had the following composition: 72% by weight of Fe, 0.06% by weight of Al, 0.03% by weight of Ca, 0.04% by weight of Mg, 0.10% by weight of Si, 0.01% by weight of Ti, 0.13% by weight of Mn, remainder oxygen.

The cooled melt block was comminuted in a jaw crusher, and a sieve fraction of particle size 1.5–3 mm was separated out by sieving. The oxidic catalyst was reduced in an $H_2/N_2$ stream at 450° C for 72 hours. After cooling down to room temperature under nitrogen, the Fe catalyst was passivated with an $N_2$/air stream (24 hours with 1% of air in nitrogen), care being taken to ensure that the temperature in the catalyst bed did not rise above 455 C b) Hydrogenation of ADN to HMD and/or ACN

Three serially connected tubular reactors (total length 4.5 m, d=6 mm) were packed with 142 mL (240 g) of the catalyst (particle size range from 1.5 to 3 mm) prepared according to Example 1a) and then reduced in a 200 L/h stream of hydrogen at atmospheric pressure. To this end, the temperature was raised from 70° C to 340° C over 24 hours and subsequently held at 340° C for 72 hours. After the temperature had been lowered, the reactor was fed with a mixture of 74 or 148 mL/h of ADN (catalyst space velocity 0.5 or 1.0 kg of ADN/L of cat.×h), 365 mL/h of $NH_3$ and 200 standard L/h of $H_2$ at 250 bar. No decrease in catalyst activity was observed after a run of 7000 hours. Under the conditions recited in Table 1, the following results were obtained as a function of the temperature and the catalyst space velocity (Table 1):

Hexamethylenediamine by Hydrogenation of Adiponitrile

| Temperature (° C.) | Pressure (bar) | Cat. space velocity (kg) | ADN conversion | HMD selectivity | ACN | ICCP | AMCPA | DCH | THA |
|---|---|---|---|---|---|---|---|---|---|
| 115 | 250 | 0.5 | 100 | 99.0 | 100 | 55 | 24 | 1150 | 30 |
| 135 | 250 | 1.0 | 100 | 98.9 | 110 | 60 | 35 | 1800 | 43 |
| 98 | 250 | 0.5 | 80 | 42.3 | 56.8[1] | 94 | 41 | 1130 | |

[1] ACN selectivity [%]

We claim:

1. A catalytically effective composition consisting of
   (a) iron or a compound based on iron or mixtures thereof,
   (b) from 0.001 to 0.3% by weight based on (a) of a promoter based on 2, 3, 4 or 5 elements selected from the group consisting of aluminum, silicon, zirconium, titanium and vanadium,
   (c) from 0 to 0.3% by weight based on (a) of a compound based on an alkali and/or alkaline earth metal, and
   (d) from 0.001 to 1% by weight based on (a) of manganese.

2. The composition defined in claim 1, characterized by a BET surface area of from 3 to 20 m²/g, a total pore volume of from 0.05 to 0.2 mL/g, an average pore diameter of from 0.03 to 0.1 μm and a 0.01 to 0.1 μm pore volume fraction within a range of from 50 to 70%.

3. The composition defined in claim 1, which is obtained by reduction with or without subsequent passivation of a magnetite.

4. The composition defined in claim 1, wherein the promoter elements of constituent (b) are selected from aluminum, silicon and titanium.

5. The composition defined in claim 1, wherein constituent (c) is based on magnesium and/or calcium.

6. The composition defined in claim 1, wherein constituent (b) comprises 3, 4 or 5 elements selected from the group consisting of aluminum, silicon, zirconium, titanium and vanadium.

7. The composition defined in claim 1, wherein constituent (b) is present in an amount of from 0.01 to 0.2% by weight based on (a).

8. The composition defined in claim 1, wherein constituent (b) is present in an amount of from 0.01 to 0.1% by weight based on (a).

9. The composition defined in claim 1, wherein the promoter elements of constituent (b) comprise aluminum, silicon and titanium.

10. The composition defined in claim 1, wherein the promoter elements of constituent (b) are aluminum, silicon and titanium.

11. The composition defined in claim 1, wherein constituent (c) is present in an amount of from 0.01 to 0.2% by weight based on (a).

12. The composition defined in claim 1, wherein constituent (c) is present in an amount of from 0.01 to 0.1% by weight based on (a).

13. The composition defined in claim 1, wherein the alkali and alkali earth metal of constituent (b) is selected from the group consiting of lithium, sodium, potassium, rubidium, cesium, magnesium and calcium.

14. The composition defined in claim 1, wherein the alkali and alkali earth metal of constituent (b) is calcium and/or magnesium.

15. The composition defined in claim 1, wherein constituent (d) is present in an amount of from 0.001 to 0.3% by weight based on (a).

16. The composition defined in claim 1, wherein constituent (d) is present in an amount of from 0.01 to 0.2% by weight based on (a).

* * * * *